United States Patent
Molenda et al.

(10) Patent No.: US 9,526,691 B2
(45) Date of Patent: *Dec. 27, 2016

(54) LEAVE-IN CONDITIONING COMPOSITION FOR HAIR

(75) Inventors: Michael Molenda, Frankfurt (DE); Normen Lipinski, Frankfurt (DE)

(73) Assignee: KAO GERMANY GMBH, Darmstadt (DE)

( * ) Notice: Subject to any disclaimer, the term of this patent is extended or adjusted under 35 U.S.C. 154(b) by 40 days.

This patent is subject to a terminal disclaimer.

(21) Appl. No.: 13/976,117

(22) PCT Filed: Dec. 27, 2011

(86) PCT No.: PCT/EP2011/074066
§ 371 (c)(1),
(2), (4) Date: Jun. 26, 2013

(87) PCT Pub. No.: WO2012/089718
PCT Pub. Date: Jul. 5, 2012

(65) Prior Publication Data
US 2013/0276808 A1 Oct. 24, 2013

(30) Foreign Application Priority Data
Dec. 30, 2010 (EP) .................... 10197379

(51) Int. Cl.
| | | |
|---|---|---|
| *A61Q 5/12* | (2006.01) | |
| *A61K 8/97* | (2006.01) | |
| *A61K 8/39* | (2006.01) | |
| *A61K 8/81* | (2006.01) | |
| *A61K 8/92* | (2006.01) | |
| *A61K 8/34* | (2006.01) | |
| *A61K 8/84* | (2006.01) | |
| *A61Q 5/10* | (2006.01) | |

(52) U.S. Cl.
CPC ................ *A61K 8/97* (2013.01); *A61K 8/342* (2013.01); *A61K 8/39* (2013.01); *A61K 8/817* (2013.01); *A61K 8/8182* (2013.01); *A61K 8/84* (2013.01); *A61K 8/922* (2013.01); *A61Q 5/10* (2013.01); *A61Q 5/12* (2013.01)

(58) Field of Classification Search
None
See application file for complete search history.

(56) References Cited

U.S. PATENT DOCUMENTS

| | | | | |
|---|---|---|---|---|
| 8,865,145 | B2 * | 10/2014 | Molenda et al. | 424/70.12 |
| 2003/0191035 | A1 * | 10/2003 | Verboom et al. | 510/119 |
| 2005/0158262 | A1 * | 7/2005 | Parris | A61K 8/416 424/70.1 |
| 2006/0140887 | A1 * | 6/2006 | Molenda et al. | 424/59 |
| 2007/0110695 | A1 * | 5/2007 | Hoffmann et al. | 424/70.12 |
| 2008/0096786 | A1 | 4/2008 | Holt et al. | |
| 2009/0041706 | A1 * | 2/2009 | Molenda et al. | 424/70.9 |
| 2009/0041709 | A1 * | 2/2009 | Hoffmann | A61K 8/731 424/70.12 |
| 2010/0028272 | A1 * | 2/2010 | Knappe | A61K 8/8152 424/47 |

FOREIGN PATENT DOCUMENTS

| | | | |
|---|---|---|---|
| EP | 1 518 537 A2 | | 3/2005 |
| EP | 2161016 | * | 3/2010 |
| FR | 2 940 072 A1 | | 6/2010 |
| GB | 2 071 495 A | | 9/1981 |

OTHER PUBLICATIONS

International Search Report mailed May 21, 2012.

* cited by examiner

*Primary Examiner* — Jyothsna Venkat
(74) *Attorney, Agent, or Firm* — Norris McLaughlin & Marcus PA

(57) ABSTRACT

Present invention relates to a leave-in conditioning composition for hair which provides hair improved combability, manageability, body, elasticity and natural softness. The object of the present invention is an aqueous composition for conditioning human hair comprising at least one lipophilic compound, at least one surfactant as a solubilizer at a concentration in the range of 0.1 to 3% by weight calculated to the total of the composition and a cationic or an amphoteric polymer with a cationic change density of at least 1.0 meq/g with the condition that the composition is substantially free of organic solvent.

11 Claims, No Drawings

LEAVE-IN CONDITIONING COMPOSITION FOR HAIR

This application is a 371 application of PCT/EP2011/074066 filed Dec. 27, 2011, which claims foreign priority benefit under 35 U.S.C. §119 of European Application No. 10197379.0 filed Dec. 30, 2010.

Present invention relates to a leave-in conditioning composition for hair which provides hair improved combability, manageability, body, elasticity and natural softness.

Leave-in conditioning compositions have been known for sometime and becoming increasingly popular because they are easy to use with no processing time and subsequent rinsing off steps and because they may be used on wet and dry hair and therefore often seen as a kind of refresher. Known compositions are either emulsion or dispersion type of non-transparent compositions or transparent compositions comprising high level of organic solvent in order to solubilize the active compounds without using too high concentrations of surfactant type of solubilizers. In case that the compositions comprise high level of surfactant solubilizers, especially nonionic surfactants, it is often observed that cosmetic properties of hair are not improved and mostly contrary is the case especially in terms of elasticity, shine and combability.

In order to achieve acceptable level of conditioning, lipophilic compounds, especially oils, have been particularly preferred. Solubilization of such in the absence of organic solvent require use of high concentration of surfactants which often result in, on one hand, high level of foaming either during application and/or especially during production and on the other hand, inacceptable conditioning. There is a need for developing new ways of obtaining transparent leave in conditioning compositions which improve cosmetic properties of hair in terms of combability, manageability, body, elasticity and natural softness and at the same time does not take away too much of shine.

The aim of the present invention is to provide a transparent conditioning composition for hair which is especially well suited for leave in usage which is substantially free of organic solvents.

The inventors of the present invention have surprisingly found out that a composition comprising lipophilic compounds, especially oil, a solubilizer preferably selected from nonionic and cationic/cationizable surfactants and a cationic or an amphoteric polymer which is substantially free of organic solvent is especially well suited for leave-in usage and improves hair cosmetic properties in terms of combability, manageability, body, elasticity and natural softness.

Accordingly the first object of the present invention is an aqueous composition for conditioning human hair comprising at least one lipophilic compound, at least one surfactant as a solubilizer at a concentration in the range of 0.1 to 3% by weight calculated to the total of the composition and a cationic or an amphoteric polymer with a cationic change density of at least 1.0 meq/g with the condition that the composition is substantially free of organic solvent.

Further object of the present invention is the use of the composition according to the present invention for conditioning hair and especially as a leave-in hair conditioner.

Still further object of the present invention is process for conditioning hair wherein a composition according to the present invention is applied and without rinsing of hair is dried or left to dry.

Another object of the present invention is a kit for treating hair comprising a composition according to the present invention.

In the preferred form of the present invention, the compositions are transparent measured by naked eye in a transparent colorless glass vessel with a thickness of at least 1 cm but not exceeding 5 cm.

Compositions of the present invention are aqueous compositions and preferably comprise at least 85%, preferably 90% more preferably 92%, most preferably 95% by weight calculated to the total of the composition water.

Compositions are substantially free of organic solvent. It should be noted that organic solvents included into composition because the used raw material one or the other way comprises such are not excluded. With the term "substantially free of organic solvent" it is meant that the compositions do not comprise any added organic solvent in order to change the physico-chemical properties of the composition and/or in order to affect the conditioning performance on hair.

Compositions of the present invention comprise at least one lipophilic compound. Preferred lipophilic compounds are the ones liquid at room temperature. Suitable ones are silicone oils, synthetic oils such as fatty acid fatty alcohol esters, mineral oil and natural oils. Natural oils are especially preferred.

Non-limiting examples to the silicone oils are volatile and non-volatile dimethicones with various viscosities as available under the trade name DC 200 series from Dow Corning, dimethiconols, polydimethylsiloxanes, cyclosiloxanes such as DC 245 and arylated silicones such as diphenyl dimethicone, diphenylsiloxy phenyl trimethicone, tetramethyl tetraphenyl trisiloxane, triphenyl trimethicone, tetramethyl tetraphenyl trisiloxane and trimethyl pentaphenyl trisiloxane.

Nonlimiting examples to synthetic oils including mineral oil such as paraffin oil and petrolatum and fatty acid fatty alcohol esters are isopropyl myristate, palmitate, stearate and isostearate, oleyl oleate, isocetyl stearate, hexyl laurate, dibutyl adipate, dioctyl adipate, myristyl myristate, oleyl erucate, and cetyl-palmitate.

Non-limiting examples to natural oils are argan oil, shea butter oil, olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin, passiflora oil, black cumin oil, borage oil, grapeseed oil, macadamia oil, rosehip oil and hempseed oil. Preferred natural oils are argan oil, shea butter oil, olive oil, almond oil, avocado oil, coconut oil, palm oil, peach kernel oil, wheat germ oil, macadamia nut oil, grape seed oil, macadamia oil and jojoba oil. Most preferred are argan oil, shea butter oil, olive oil, almond oil, avocado oil, peach kernel oil, wheat germ oil, macadamia nut oil, grape seed oil, macadamia oil and jojoba oil.

Concentration of at least one oil in the compositions of the present invention is in the range of 0.001 to 1%, preferably 0.005 to 0.75%, more preferably 0.01 to 0.5% and in particular 0.01 to 0.4% by weight calculated t the total of the composition.

Composition of the present invention comprises at least one surfactant as a solubilizer. In particular any surfactant with solubilising capacity is suitable for the compositions. Preferred surfactants are non-ionic and cationic/cationizable surfactants.

Preferably the non-ionic surfactants are selected from the ones with reduced foaming power. Preferred are fatty alcohol ethoxylates according to the general structure

$$R_1(OCH_2CH_2)_nOH$$

wherein $R_1$ is a straight or branched, saturated or unsaturated alkyl chain with 12 to 24 C atoms which may be substituted with one or more hydroxyl groups and n is a number between 5 and 200, and ethoxylated glycerides according to the general structure

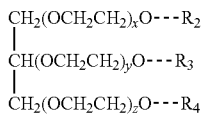

wherein $R_2$ to $R_4$ may be same or different is H or a straight or branched, saturate or unsaturated fatty acyl group which may be substituted with one or more hydroxyl groups with a chain length of 10 to 24 C atoms, preferably 12 to 18 C atoms, with the condition that at least one of the $R_2$ to $R_4$ is different from H and x, y and z are a number between 0 and 1000, preferably 0 to 250, with the condition that the sum of the x, y and z is in the range of 0 to 1000, preferably 20 to 250.

Non-limiting examples to fatty alcohol ethoxylates are C12-13 Pareth-7, C12-13 Pareth-9, C12-13 Pareth-10, C12-13 Pareth-15, C12-13 Pareth-23, Ceteareth-20, Ceteareth-30, Steareth-20, Steareth-30, Ceteth-20, Ceteth-25, Ceteth-30, Ceteth-35, Ceteth-40, Oleth-10, Oleth-20, Oleth-25, Oleth-30, Oleth-35, Oleth-40, Oleth-50 and Oleth-100.

Nonlimiting examples to ethoxylated glycerides are PEG-30 glyceryl cocoate, PEG-80-glycerylcocoate, PEG-80-glyceryl tallowate, PEG-120-glyceryl stearate, PEG-200-glyceryl stearate, PEG-200-glyceryl tallowate, hydrogenated PEG-200-glyceryl palmitate, PEG-250 2-octyldodecanol, PEG-100 stearyl alcohol, PEG-50 oleyl alcohol, PEG 50 EO dioleate, PEG-200 glycerol palmitate, PEG-150 stearate, PEG-120 dioleate, PEG-55 dioleate, PEG-300 undecylenate, PEG-150 distearate, PEG-7 glycerol monoundecylenate, PEG-15 glycerol monostearate, PEG-20 glycerol monolaurate, PEG-20 glycerol dilaurate, PEG-4 glycerol stearate, PEG-7 glycerol cocoate, PEG-25 glycerol monoisostearate, PEG-20 glycerol monostearate, PEG-30 glycerol monostearate, PEG-20 monostearate, PEG-6 laurate, PEG-8 distearate, PEG-8 dilaurate, PEG-8 monooleate, PEG-8 dioleate, PEG-30 distearate, PEG-40 stearate, PEG-20 Hydrogenated castor oil, PEG-20 Hydrogenated castor oil, PEG-20 Hydrogenated castor oil, PEG-25 Hydrogenated castor oil, PEG-30 Hydrogenated castor oil, PEG-35 Hydrogenated castor oil, PEG-40 Hydrogenated castor oil, PEG-45 Hydrogenated castor oil, PEG-50 Hydrogenated castor oil, PEG-54 Hydrogenated castor oil, PEG-55 Hydrogenated castor oil, PEG-60 Hydrogenated castor oil, PEG-65 Hydrogenated castor oil, PEG-80 Hydrogenated castor oil, PEG-100 Hydrogenated castor oil, and PEG-200 Hydrogenated castor oil.

Preferred are C12-13 Pareth-7, C12-13 Pareth-9, C12-13 Pareth-10, C12-13 Pareth-15, C12-13 Pareth-23, Hydrogenated castor oil, PEG-25 Hydrogenated castor oil, PEG-30 Hydrogenated castor oil, PEG-35 Hydrogenated castor oil, PEG-40 Hydrogenated castor oil, PEG-45 Hydrogenated castor oil, PEG-50 Hydrogenated castor oil, PEG-54 Hydrogenated castor oil, PEG-55 Hydrogenated castor oil, PEG-60 Hydrogenated castor oil.

Concentration of nonionic surfactant varies in the range of 0.05 and 2%, preferably 0.05 to 1.5%, more preferably 0.05 to 1% and most preferably 0.1 to 1% by weight calculated to the total of the composition.

Preferably cationic surfactants are selected from the compounds according to the general structure

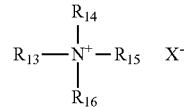

where $R_{13}$ is a saturated or unsaturated, branched or straight alkyl chain with 10-24 C atoms or

where $R_{17}$ is saturated or unsaturated, branched or straight alkyl chain with 7-21 C atoms and n has value of 1-4, or

where $R_{18}$ is saturated or unsaturated, branched or straight alkyl chain with 7-21 C atoms and n has value of 1-4, and $R_{14}$ is unsaturated or saturated, branched or straight alkyl chain with 1-24 C atoms or

or

where $R_{17}$, $R_{18}$ and n are same as above, $R_{15}$ and $R_{16}$ are independent from each other lower alkyl chain with 1 to 4 carbon atoms which may be substituted with one or more hydroxyl groups, and X is anion such as chloride, bromide, methosulfate.

In the preferred embodiment of the present invention $R_{14}$ is a lower alkyl chain with 1 to 4 carbon atoms which may be substituted with one or more hydroxyl groups.

Cationizable surfactants are according to the general structure

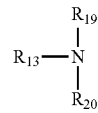

where $R_{13}$ is same as above, and $R_{10}$ and $R_{20}$ are independent from each other H, lower alkyl chain with 1 to 4 carbon atoms which may be substituted with one or more hydroxyl groups.

With the term cationizable surfactant it is meant that the surfactant becomes cationic by protonation.

Non-limiting suitable examples are cetyl trimethyl ammonium chloride, steartrimonium chloride, behentrimonium chloride, stearamidopropyl trimonium chloride, palmitamidopropyltrimonium chloride, stearamidopropyldimethyl amine, palmitamidopropyldimethyl amine.

Concentration of cationic/cationizable surfactant varies in the range of 0.05 and 2%, preferably 0.05 to 1.5%, more preferably 0.05 to 1% and most preferably 0.1 to 1% by weight calculated to the total of the composition.

In the preferred embodiment of the present invention, composition comprises at least one nonionic surfactant and at least one cationic/cationizable surfactant. Total surfactant concentration in the compositions is in the range of 0.1 and 3%, preferably 0.1 to 2.5%, more preferably 0.2 to 2% and most preferably 0.2 to 1.5% by weight calculated to the total of the composition.

Composition comprises at least one a cationic or an amphoteric polymer with a cationic change density of at least 1.0 meq/g. Cationic charge density may be calculated as the number of cationic charges divided by molecular weight of the monomer unit or average molecular weight of monomer units and multiplied by 1000 in order to express it as meq/g. It may also be measured with a method according to Kjeldahl.

Preferably cationic charge density is at least 2 meq/g and more preferably 3 meq/g and in particular 3.5 meq/g.

Suitable cationic polymers are Polyquaternium-6, Polyquaternium-7, Polyquaternium-16 and polyquaternium-39 is the preferred amphoteric polymer.

Particularly preferred polymers are cationic polymers with charge density of at least 3.5 meq/g which are know as Polyquaternium-6 with a charge density of 6.2 meq/g and Polyquaternium-16 with a charge density of 6.1 meq/g.

Concentration of cationic or amphoteric polymer in the compositions is in the range of 0.05 and 2%, preferably 0.05 to 1.5%, more preferably 0.1 to 1% by weight calculated to the total of the composition.

Composition of the present invention can comprise one or more of the following ingredients.

Compositions may comprise one or more of hair conditioning and/or styling polymers. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water- or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives or Polyurethanes such as "Baycusan®" Types, distributed by Bayer AG.

The UV filters are of oil and water soluble ones for the purpose of protecting hair and hair colour. In other words, anionic and non-ionic, oily, UV filters are suitably used in the compositions of the present invention. Suitable UV-absorbing substances is are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher, and/or polysilicone-15. The concentration of the UV-absorber ranges typically from about 0.01% to 2.5%, more preferably from 0.05% to 1% by weight, calculated to the total of the composition.

Natural plant extracts are incorporated usually in an amount of about 0.01% to about 1%, preferably 0.05% to 0.75%, in particular 0.1% to 0.5% by weight, calculated as dry residue thereof to the total composition. Suitable aqueous (e.g. steam-distilled) extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, various "Extrapone®" products, and "Herbasol®". Extracts and the preparation thereof are also described in "Hagers Handbuch der pharmazeutischen Praxis", 4$^{th}$ Ed. It must be noted that these extracts may comprise organic solvents and therefore organic solvent may be comprised in the compositions of the present invention.

Compositions of the present invention may comprise further at least one compound according to the formula

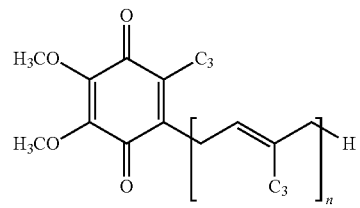

where n is a number from 1 to 10.

The compounds of the above formula are known as Ubiquinone, and also are known as Coenzyme. It should be noted that the compositions of the present invention can certainly comprise more than one ubiquinone. Preferred ubiquinones are the ones where n is a number between 6 and 10 and especially preferred is Ubiquinone 50 where n is 10, also known as Coenzyme Q10. Concentration ubiquinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $$R_{30}CO(OCH_2CH_2)_nOH \text{ or}$$

$$R_{30}CO(OCH_2CH_2)_nOOCR_{31}$$

where $R_{30}$ and $R_{31}$ are independent from each other saturated, unsaturated or branched or non-branched alkyl chain with 7 to 21 C atoms and n is typically 2-100. Concentration of such compounds is usually less than 1%, preferably less than 0.5% by weight calculated to the total of the compositions. The compounds mentioned here must not be taken as solvent because of their low concentration. In any case use purpose of these compounds is not because of their solvent properties but because of their conditioning and/or moisturising effect.

Further in a preferred embodiment of the present invention, compositions comprise at least one direct dye and as well deposit dyestuffs on the hair. Suitable direct dyes are of cationic, anionic and neutral nitro dyes. It should be noted that they can also be used in combination with each other. In other words a composition according to present invention can comprise an anionic and a cationic dye as well as an anionic and a nitro dye or a cationic and a nitro dye. Certainly the combination of all three dyestuff categories is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, HC Blue No 17 and mixtures thereof Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and mixtures thereof.

Among those, the preferred anionic dyestuffs are Acid Red 52, Acid Violet 2, Acid Red 33, Acid Orange 4, Acid Red 27 and Acid Yellow 10 and their salts, and mixtures thereof. The most preferred anionic dyes are Acid Red 52, Acid Violet 2, Acid Red 33, Acid Orange 4 and Acid Yellow 10, and their salts, and mixtures thereof.

Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and mixtures thereof.

Concentration of one or more direct dyes in total is in the range of 0.0001 to 1% by weight, preferably 0.001 to 0.75% more preferably 0.005 to 0.5% and most preferably 0.01 to 0.5% by weight calculated to total composition. The most preferred among the direct dyes is cationic direct dyes.

The pH of the compositions according to the present invention is suitably between 2 and 8.0, preferably in the range of 2.5 to 7.0, more preferably 3 to 6.5 and most preferably 4 to 6.0 measured at ambient temperature with a suitable pH meter.

pH of the compositions is adjusted with acidic and alkaline compounds. Acidic compounds can be inorganic and organic acid or their mixtures. Nonlimiting suitable examples are citric acid, lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. Alkaline compounds such as sodium hydroxide can be used to adjust the pH of the compositions.

Viscosity of the compositions as measured with a capillary viscosimeter or a suitable another method at 20° C. is below 1000 mPa·s, preferably 500 mPa·s.

Compositions of the present invention may be applied from a bottle with a nozzle directly onto hair and also may be sprayed onto hair from a bottle equipped with a spraying pump. In another form of the present invention compositions may be applied from an aerosol container which then comprises additionally pressurizing volatile compounds which may be selected from alkanes and/or haloalkanes or dimethyl ether.

Following examples are to illustrate the invention but not to limit it.

EXAMPLE 1

|  | % by weight |
| --- | --- |
| Argan oil | 0.1 |
| C12-13 Pareth-9 | 0.8 |
| Polyquaternium-6 | 0.4 |
| Fragrance | 0.05 |
| Lactic acid/sodium hydroxide | q.s. to pH 5.5 |
| Water | q.s. to 100 |

Above composition was prepared by dissolving argan oil and fragrance in solution of non-ionic surfactant and combining it with cationic polymer and water and after adjusting the pH the reaming water was added. Composition was transparent.

The above composition was applied onto freshly washed and towed dried hair and dried with a hair drier. It was observed tat hair was easily combable, had natural elasticity and softness. Shine was not very much affected by the application of the composition. Removal of Polyquaternium-6 resulted in loss of effects. In the same way removal of argan oil also resulted in loss of effects.

Similar results were observed with the following examples. All compositions were prepared in the same way as disclosed above.

EXAMPLE 2

|  | % by weight |
| --- | --- |
| Argan oil | 0.1 |
| Cetrimonium chloride | 1.0 |
| Polyquaternium-6 | 0.2 |
| Fragrance | 0.05 |
| Lactic acid/sodium hydroxide | q.s. to pH 5.5 |
| Water | q.s. to 100 |

EXAMPLE 3

| | % by weight |
|---|---|
| Shea butter oil | 0.1 |
| PEG-40 hydrogenated castor oil | 0.5 |
| Polyquaternium-16 | 0.5 |
| Fragrance | 0.05 |
| Lactic acid/sodium hydroxide | q.s. to pH 5.0 |
| Water | q.s. to 100 |

EXAMPLE 4

| | % by weight |
|---|---|
| Macadamia nut oil | 0.1 |
| PEG-40 hydrogenated castor oil | 0.5 |
| Cetrimonium chloride | 0.5 |
| Polyquaternium-6 | 0.5 |
| Fragrance | 0.05 |
| Lactic acid/sodium hydroxide | q.s. to pH 5.0 |
| Water | q.s. to 100 |

EXAMPLE 5

| | % by weight |
|---|---|
| Argan oil | 0.1 |
| C12-13 Pareth-9 | 0.8 |
| Polyquaternium-6 | 0.4 |
| VP/VA copolymer | 1.0 |
| Fragrance | 0.05 |
| Lactic acid/sodium hydroxide | q.s. to pH 5.5 |
| Water | q.s. to 100 |

EXAMPLE 6

| | % by weight |
|---|---|
| Argan oil | 0.1 |
| C12-13 Pareth-9 | 0.6 |
| Behentrimonium chloride | 0.3 |
| Polyquaternium-6 | 0.4 |
| VP/VA copolymer | 1.0 |
| Basic red 51 | 0.05 |
| Basic orange 31 | 0.01 |
| Basic yellow | 0.02 |
| Fragrance | 0.05 |
| Lactic acid/sodium hydroxide | q.s. to pH 5.5 |
| Water | q.s. to 100 |

EXAMPLE 7

| | % by weight |
|---|---|
| Argan oil | 0.1 |
| C12-13 Pareth-9 | 0.6 |
| Behentrimonium chloride | 0.3 |
| Polyquaternium-6 | 0.4 |
| VP/VA copolymer | 1.0 |
| Basic red 51 | 0.05 |
| Basic orange 31 | 0.01 |
| Benzophenone-3 | 0.02 |
| Fragrance | 0.05 |
| Lactic acid/sodium hydroxide | q.s. to pH 5.5 |
| Water | q.s. to 100 |

EXAMPLE 8

| | % by weight |
|---|---|
| Argan oil | 0.1 |
| C12-13 Pareth-9 | 0.6 |
| Behentrimonium chloride | 0.3 |
| Polyquaternium-6 | 0.4 |
| VP/VA copolymer | 1.0 |
| Basic red 51 | 0.05 |
| HC Blue 17 | 0.02 |
| HC red 3 | 0.02 |
| Benzophenone-3 | 0.02 |
| Fragrance | 0.05 |
| Lactic acid/sodium hydroxide | q.s. to pH 5.5 |
| Water | q.s. to 100 |

The invention claimed is:

1. An aqueous composition for conditioning human hair, the aqueous composition comprising
   argan oil,
   at least one surfactant as a solubilizer at a concentration in the range of 0.1 to 3% by weight calculated to the total of the composition, and
   a cationic or an amphoteric polymer with a cationic change density of at least 1.0 meq/g with the proviso that the composition is substantially free of organic solvent,
   wherein the at least one surfactant is selected from at least one non-ionic surfactant and at least one cationic/cationizable surfactant, the at least one non-ionic surfactant is selected from the group consisting of PEG-25 Hydrogenated castor oil, PEG-30 Hydrogenated castor oil, PEG-35 Hydrogenated castor oil, PEG-40 Hydrogenated castor oil, PEG-45 Hydrogenated castor oil, PEG-50 Hydrogenated castor oil, PEG-54 Hydrogenated castor oil, PEG-55 Hydrogenated castor oil, PEG-65 Hydrogenated castor oil, PEG-80 Hydrogenated castor oil, PEG-100 Hydrogenated castor oil, and PEG-200 Hydrogenated castor oil, and the at least one cationic/cationizable surfactant is selected from the group consisting cetyl trimethyl ammonium chloride, steartrimonium chloride, behentrimonium chloride, stearamidopropyl trimonium chloride, palmitamidopropyltrimonium chloride, stearamidopropyldimethyl amine and palmitamidopropyldimethyl amine, and
   further wherein the aqueous composition comprises at least 90% by weight water, calculated to the total of the composition and is transparent measured by naked eye in a transparent colorless glass vessel with a thickness of at least 1 cm but not exceeding 5 cm.

2. The aqueous composition according to claim 1, wherein the composition comprises at least 92% by weight water, calculated to the total of the composition.

3. The aqueous composition according to claim 1, wherein the argan oil is present at a concentration of 0.001 to 1% by weight calculated to the total of the composition.

4. The aqueous composition according to claim 1, wherein the composition comprises both the at least one non-ionic surfactant and the at least one cationic/cationizable surfactant.

5. The aqueous composition according to claim 1, wherein the cationic or the amphoteric polymer with a cationic change density of at least 2.0 meq/g is selected from the group consisting of Polyquaternium-6, Polyquaternium-7, Polyquaternium-16 and polyquaternium-39.

6. The aqueous composition according to claim 5, wherein the cationic polymer is selected from Polyquaternium-6 and Polyquaternium-16 and is present at a concentration of 0.05 and 2%, by weight calculated to the total of the composition.

7. The aqueous composition according to claim 1, further comprising one or more of the following ingredients
styling polymer,
UV filter,
Natural plant extract,
Ubiquinone, and
Direct dye selected from cationic, anionic and neutral dyes.

8. The aqueous composition according to claim 1, wherein the composition has a viscosity below 1000 mPa·s measured at 20° C. with a capillary viscosimeter.

9. The aqueous composition according to claim 2, wherein the composition at least 95% by weight water, calculated to the total of the composition.

10. The aqueous composition according to claim 1, wherein the at least one surfactant consists of the at least one non-ionic surfactant present at a concentration of 0.05-0.8% by weight, calculated to the total of the composition.

11. The aqueous composition according to claim 1, wherein the at least one surfactant consists of the at least one non-ionic surfactant and the at least one cationic/cationizable surfactant, wherein the at least one non-ionic surfactant is present at a concentration of 0.05-0.8% by weight, calculated to the total of the composition, and the at least one cationic/cationizable surfactant is present at a concentration of 0.05-0.5% by weight, calculated to the total of the composition.

* * * * *